United States Patent [19]
Bäckström et al.

[11] Patent Number: 5,889,037
[45] Date of Patent: Mar. 30, 1999

[54] PHARMACOLOGICALLY ACTIVE CATECHOL DERIVATIVES

[75] Inventors: Reijo Bäckström, Helsinki; Erkki Honkanen, Espoo; Inge-Britt Linden, Helsinki; Erkki Nissinen, Espoo; Aino Pippuri, Espoo; Pentti Pohto, Espoo; Tapio Korkolainen, Helsinki, all of Finland

[73] Assignee: Orion-yhtymä Oy, Espoo, Finland

[21] Appl. No.: 472,658

[22] Filed: Jun. 7, 1995

Related U.S. Application Data

[62] Division of Ser. No. 325,024, Oct. 18, 1994, Pat. No. 5,614,541, which is a division of Ser. No. 949,477, filed as PCT/FI91/00124, Apr. 26, 1991, Pat. No. 5,362,733.

[30] Foreign Application Priority Data

| Apr. 27, 1990 | [GB] | United Kingdom | 9009565 |
| Jan. 24, 1991 | [GB] | United Kingdom | 9101563 |

[51] Int. Cl.⁶ .............. A61K 31/415; C07D 233/78; C07D 233/86; C07D 233/96
[52] U.S. Cl. .............. 514/389; 548/317.1; 548/318.1; 548/321.5
[58] Field of Search .............. 548/317.1, 321.5, 548/318.1; 514/389

[56] References Cited

U.S. PATENT DOCUMENTS

| 4,013,770 | 3/1977 | Bharucha | 514/389 |
| 4,241,073 | 12/1980 | Jamieson et al. | 514/389 |
| 4,264,617 | 4/1981 | Bharucha et al. | 514/389 |
| 4,345,072 | 8/1982 | Kleemann et al. | 548/311.7 |
| 4,376,777 | 3/1983 | Kawamatsu et al. | 514/369 |

(List continued on next page.)

FOREIGN PATENT DOCUMENTS

| 0 032 128 | 7/1981 | European Pat. Off. . |
| 0 037 479 | 10/1981 | European Pat. Off. . |
| 0 037 480 | 10/1981 | European Pat. Off. . |
| 0 343 643 | 11/1989 | European Pat. Off. . |
| 0 211 670 | 5/1990 | European Pat. Off. . |

OTHER PUBLICATIONS

Studies on Styrene Derivatives. Ikuo Katsumi et al, *Chem. Pharm. Bull.*, 1986, 34(4), 1619–1627.

Chemical Abstracts, vol. 95, Page 202 (1977). Entry 87:2312y, "L–Amino Acids", by Sano Konosuke et al..

Chemical Abstracts, vol. 95, Page 731 (1981). Entry 95;169070v, "Synthesis, transformation, spectral and analytical characterization of 2–thiohydantoin derivatives from (—) —3—(3,4—dihydroxyphenyl)–L–alanine", by v. G. Zubenko et al.

"Autoxidation of Micelles and Model Membranes, Quantitative Kinetic Measurements Can Be Made By Using Either Water–Soluble or Lipid–Soluble Initiators With Water–Soluble or Lipid–Soluble Chain Breaking Antioxidants", L.R.C. Barclay, et al., J. Am. Chem. Soc. 1984, 106 pp. 2479–2481.

"Free Radical Chain Oxidation of Rat Red Blood Cells by Molecular Oxygen and its Inhibition by α–Tocopheral", Masayuki Miki et al., Archives of Biochemistry and Biophysics, vol. 258, No. 2, Nov. pp. 373–380 (1987).

"the Anti–Inflammatory Effects of LY 178002 and LY 256548", J.A. Paneta et al., (Lilly Res. Lab., Eli Lilly and Co.), Agents Actions 1989, 27 (3–40, 300–2 (Eng.) CA 111:3306t.

"Two Anti–Oxidants, LY 178002 and LY 256548, as therapies for Three Unrelated Degenerative Diseases", J.A. Panetta et al., Oxid. Damage Repair, (Int. soc. Free Radical Res. Bienn Meeting) 5th 1990, CA 117;204769b.

Stein, Jay H., *Internal Medicine*, Fourth Edition, Mosby, St. Louis, 1994.

Vapaatalo, H. *Medical Biology*, vol. 64, p. 1; abstract only via MEDLINE (1986).

Hatherill, J.R. *Agents and Actions*, vol. 32, p. 351; abstract only via MEDLINE (Mar. 1991).

Turrens, J.F. *Xenobitica*, vol. 21, p. 1033; abstract only via MEDLINE (Aug. 1991).

*Primary Examiner*—Mukund J. Shah
*Assistant Examiner*—Ann M. Kessinger
*Attorney, Agent, or Firm*—Burns, Doane, Swecker & Mathis, L.L.P.

[57] ABSTRACT

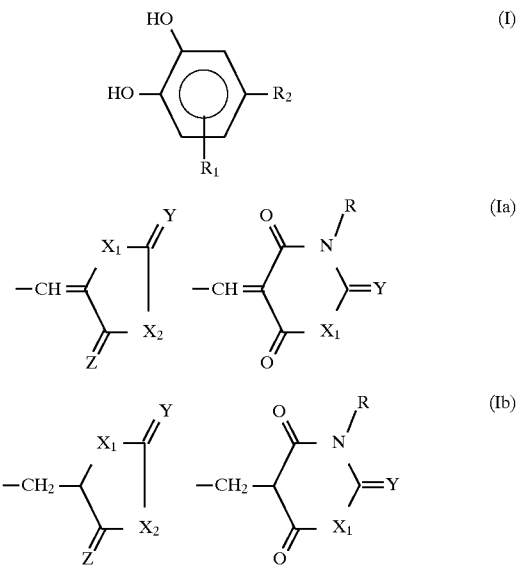

Compounds of formula (I), wherein $R_1$ is an electronegative substituent such as nitro, halogeno or cyano group and $R_2$ is a group selected from (Ia) and (Ib), wherein R is hydrogen, or an alkyl, cycloalkyl, aralkyl or aryl group, wherein $X_1$, $X_2$, Y and Z are independently oxygen, sulfur of NR, wherein R may be as defined above and pharmaceutically acceptable esters and salts thereof are useful in the prevention or treatment of tissue damage induced by lipid peroxidation.

2 Claims, No Drawings

U.S. PATENT DOCUMENTS

| | | | |
|---|---|---|---|
| 4,582,903 | 4/1986 | Mirviss | 544/139 |
| 4,650,876 | 3/1987 | Mirviss | 548/308 |
| 4,672,127 | 6/1987 | Tanaka et al. | 548/308 |
| 5,043,354 | 8/1991 | Tsujii et al. | 514/469 |
| 5,208,250 | 5/1993 | Cetenko et al. | 514/369 |

FOREIGN PATENT DOCUMENTS

| | | |
|---|---|---|
| 2189040 | 1/1974 | France . |
| 2585701 | 2/1987 | France . |
| 1 038 050 | 2/1959 | Germany . |
| 1434074 | 4/1976 | United Kingdom . |
| 1439318 | 6/1976 | United Kingdom . |

PHARMACOLOGICALLY ACTIVE CATECHOL DERIVATIVES

This application is a divisional of application Ser. No. 08/325.024, filed Oct. 18, 1994, now U.S. Pat. No. 5,614,541, which is a divisional of application Ser. No. 07/949,477, filed Oct. 23, 1992, now U.S. Pat. No. 5,362,733, and which corresponds to PCT/FI91/00124, filed Apr. 26, 1991.

The invention relates to new catechol derivatives and pharmaceutically acceptable salts and esters thereof which are useful as medicinal antioxidants. The invention also relates to pharmaceutical compositions containing said compounds and to the method of the preparation of the same.

Medicinal antioxidants are compounds that may be used for the prevention or treatment of tissue damage induced by lipid peroxidation. It is generally believed that cellular damage by oxygen derived radicals, especially those associated with lipid peroxidation, is a significant factor in heart diseases, rheumatoid arthritis, cancer, certain inflammatory diseases, rejection reactions in transplantation, ischemia and even in the aging process.

EP-A-343643 describes pharmaceutical compositions comprising the compounds of formula

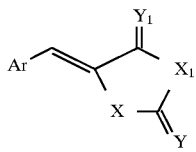

wherein Ar is (i) phenyl unsubstituted, (ii) pheonyl substituted by from one to three of lower alkyl, lower alkoxy, hydroxy, halogen, trifluoromethyl, $NR_{10}R_{11}$, wherein $R_{10}$ and $R_{11}$, are independently hydrogen or lower alkyl, $NO_2$, mercapto, or lower alkylthio, (iii) naphthyl; (iv) benzofuranyl, (v) benzothiophenyl, (vi) 2- or 3-thienyl, (vii) 2- or 3-indolyl, (viii) 2- or 3-furanyl, or (ix) 2-, 3-, or 4-pyridyl Y and $Y_1$ is oxygen or sulfur; X is sulfur, oxygen, NH or $NCH_3$ and $X_1$ is NH or $NCH_3$ and pharmaceutically acceptable salts thereof which are stated to be 5-lipoxygenase and/or cycloozygenase inhibitors. Japanese patent application No. 1052765, which has been referred to in Chemical Abstracts (CA 111(17)153788y) discloses thiazolidinone derivatives which are useful as aldose reductase inhibitors. Gupta et al. in Eur. J. Med. Chem.—Chim. Ther., 17 (5), 448–52, 1982 and Srivastava et al. in Pharmazie, 36(4), 252–3, 1981 disclose 2-thioxo-4,6-pyrimidinedione compounds having anticonvulsant activity. Sohda et al. in Chem. Pharm. Bull., 31(2), 560–9, 1983 discloses 2,4-thioxolidione derivatives having antiulcer activity.

The compounds of the present invention may be represented by the formula I

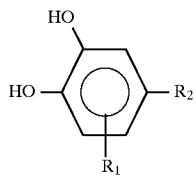

wherein $R_1$ is an electronegative substituent such as nitro, halogeno or cyano group and $R_2$ is a group selected from

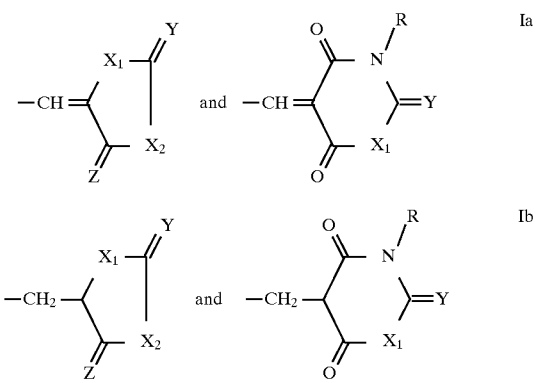

wherein R is hydrogen, or an alkyl, cycloalkyl, aralkyl or aryl group, wherein $X_1$, $X_2$Y and Z are independently oxygen, sulfur or NR wherein R may be as defined above. In one embodiment, $R_2$ is a group containing a five membered heterocyclic ring which is of formula

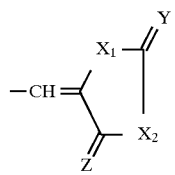

in which $X_1$ and $X_2$ are both NR, wherein R is hydrogen or alkyl, Y is oxygen or sulfur and Z is oxygen or sulfur. Preferred ring systems include 2-thioxoimidazolidin-5-ones and 2,5-imidazolidin-5-ones. Examples of such compounds. include 4-[(3,4-dihydroxy-5-nitrophenyl)methylidene]-2-thioxoimidazolidin-5-one; 4-[(3,4-dihydroxy-5-chlorophenyl)-mothylidene]-2-thioxoimidazolidin-5-one; 4-[(3,4-dihydroxy-5-nitrophenyl)methylidene]-2,5-imidazolidindione and 4-[(3,4-dihydroxy-5-cyanophenyl) methylidene]-2-thioxoimidazolidin-5-one.

In another embodiment $R_2$ is the group

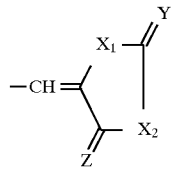

in which $X_1$, Y, and Z are independently oxygen or sulfur and $X_2$ is NR, in which R is hydrogen or alkyl. Preferred ring systems include 2-thioxothiazolidin-4-ones; 3-methyl-2-thioxothiazolidin-4-ones; thiazolidin-2,4-diones; 4-thioxo-2-oxazolidinones and 4-thioxithiazolidin-2-ones. Specific examples are 5-[(3,4-dihydroxy-5-nitrophenyl)-methylidene]-2-thioxothiazolidin-4-one; 5-[(3,4-dihydroxy-5-nitrophenyl)methylidene]-3-methyl-2-thioxothiazolidin-4-one; 5-[(3,4-dihydroxy-5-nitrophenyl)methylidene]-thiazolidin-2,4-dione; 5-[(3,4-dihydroxy-5-chlorophenyl) methylidene]-thiazolidin-2,4-dione; 5-[(3,4-dihydroxy-5-nitrophenyl) methylidene]-4-thioxo-2-oxazolidinone; 5-[(3,4-dihydroxy-5-nitrophenyl)methylidene]-4-thioxothiazolidin-2-one and 5-[(3,4-dihydroxy-5-cyanophenyl)-methylidene]-2-thioxothiazolidin-4-one.

In another embodiment $R_2$ is the group

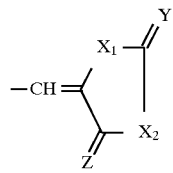

in which $X_1$ and Z are independently oxygen or sulfur and Y and $X_2$ are NR, wherein R is hydrogen. Preferred ring system is 2-aminothiazolidin-4-one. A specific example is 5-[(3,4-dihydroxy-5-nitrophenyl)methylidene]-2-aminothiazolidin-4-one.

In another embodiment $R_2$ is a group containing a six-membered heterocyclic ring which is of formula:

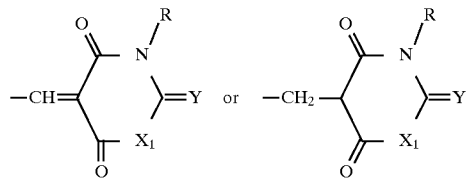

wherein Y is oxygen or sulfur, $X_1$ is NR, wherein R is hydrogen or alkyl. Preferably Y is oxygen. Preferred ring systems include pyrimidine-2,4-6-trione. Examples of such compounds include 5-[(3,4-dihydroxy-5-nitrophenyl) methylidene]-2,4,6 (1H,3H,5H)-pyrimidinetrione and 5-[(3,4-dihydroxy-5-nitrophenyl)methyl]-(1H,3H,5H)-pyrimidine-2,4,6-trione.

The term "alkyl" as employed herein by itself or as part of another group refers to both straight and branched chain groups, preferably of 1 to 8 atoms, most preferably of 1 to 4 carbon atoms.

The term "aryl" as employed herein refers to a monocyclic or bicyclic group containing 6 or 10 carbon atoms in the ring portion. A specific example is phenyl.

The term "acyl" as employed herein refers to alkylcarbonyl group, the alkyl group being as defined above.

The term "aroyl" refers to an arylcarbonyl group, the aryl group being defined above.

The term "cycloalkyl" as employed herein refers to saturated cyclic hydrocarbon groups having preferably 5 to 7 carbon atoms.

The term "halogeno" as employed herein refers to fluoro, chloro, bromo or iodo substituent. Especially preferred is chloro.

If R is hydrogen the compounds of the present invention may exist also in the corresponding tautomeric forms depending on the pH of the solution Thus, when $R_2$ is a five-membered ring, when $X_1$ is NR wherein R is hydrogen the tautomeric forms of the compounds according to formula Ia are

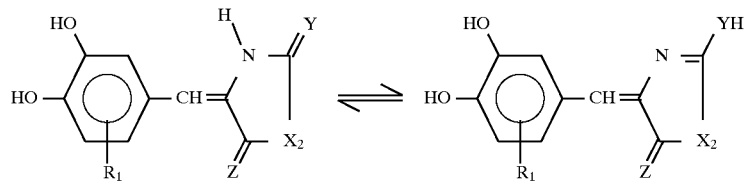

and the tautomers, when $X_2$ is NR wherein R is hydrogen are

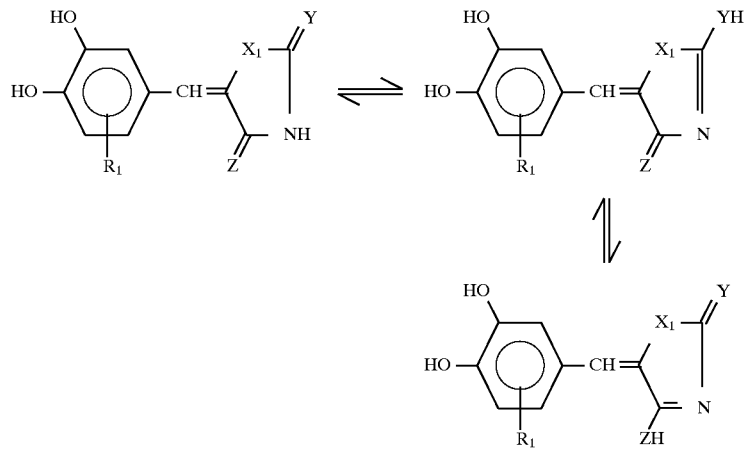

The tautomeric forms for the compounds wherein $R_2$ is a six membered ring are respectively

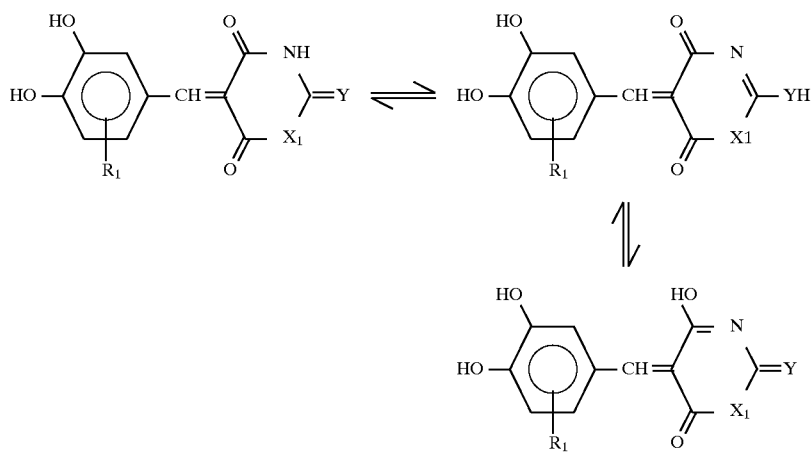

The present invention also relates to the method for the preparation of compounds of formula I. The present invention provides a process for the preparation of compounds of formula I, in which process an aldehyde of formula II

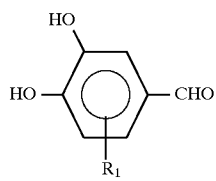

wherein $R_1$ is as defined above, is condensed in a bass or acid catalyzed reaction with compounds of either formulas III or IV having an active methylene group

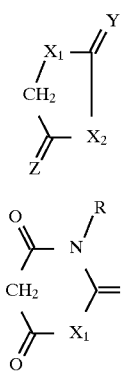

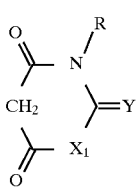

wherein $X_1$, $X_2$, Y and Z are as defined above, to give a compound Ia according to the present invention, whereafter the carbon-carbon double bond in Ia may be reduced to give the compound Ib according to the invention.

The invention also relates to pharmaceutically acceptable salts and esters of the present compounds. Generally, the esters which hydrolyze readily in physiological circumstances are those attached to the phenolic hydroxyl groups in compounds according to formula I. Either one of the hydroxylic groups or both of them may be esterified and on hydrolyzing the ester-forming group or groups are cleaved away and the active compound is liberated. Preferred esters are acyl or aroyl derivatives.

Salts of the compounds, when applicable, may be prepared by known methods. Physiologically acceptable salts are useful as active medicaments. However, sodium, potassium, ammonium, calcium and magnesium salts are preferred.

The effective dose of the compound varies considerably depending on whether the compounds are given for prophylaxis or for treatment, the severity of the condition to be treated, and the route of administration. The effective dose for human beings is likely to be from about 1 to 1000 mg per day.

The compounds used in this invention are formulated into dosage forms using the principles which are known to the man having average skill in the art. The compounds according to this invention are given to a patient as such or in combination with suitable pharmaceutical material in the form of tablets, dragoes, capsules, suppositories, emulsions, suspensions or solutions whereby the content of the active compound is in the formulation from 1 to 100 weight %.

Choosing the auxiliary ingredients for the formulation is routine for those of ordinary skill in the art. It is evident that suitable solvents, gel forming ingredients, dispersion forming ingredients, colors etc are used in a normal way.

The compositions may be administered enterally or parenterally.

Test results

Radical trapping capacity of compounds

The tested compounds were subjected to controlled peroxidation by peroxylradicals originating from the thermal decomposition of 2,2'-azobis-(2-amidinopropane)×HCl at 37° C. The rate of radical formation was followed by luminol enhanced chemiluminescence (CL). From the duration of CL and from the fact that the phenolic antioxidant vitamin E analogue TROLOXR® traps two radicals (Barclay,L. et al., J. Am. Chem. Soc. 106: 2479–2481, 1984) the stochiometric factors were calculated. The results are presented in Table 1.

TABLE 1

| The binding of peroxyl radicals by various test compounds | |
|---|---|
| Compound | Stochiometric factor |
| 1 | 7.1 |
| 2 | 5.6 |
| 3 | 4.7 |
| 4 | 4.4 |
| 5 | 4.2 |
| 6 | 4.0 |
| 7 | 4.0 |

TABLE 1-continued

The binding of peroxyl radicals by various test compounds

| Compound | Stochiometric factor |
|---|---|
| TROLOX | 2.0 |
| Ascorbic acid | 0.7 |

1 4-[(3,4-dihydroxy-5-chlorophenyl)methylidene]-2-thioxo-imidazolidin-5-one
2 5-[(3,4-dihydroxy-5-cyanophenyl)methylidene]-2-thioxo-thiazolidin-4-one
3 4-[(3,4-dihydroxy-5-nitrophenyl)methylidene]-2,5-imid-azolindione
4 5-[(3,4-dihydroxy-5-nitrophenyl)methylidene]-2-thioxo-thiazolidin-4-one
5 4-[(3,4-dihydroxy-5-nitrophenyl)methylidene]-2-thioxo-imidazolidin-5-one
6 5-[(3,4-dihydroxy-5-nitrophenyl)methylidene]-2,4,6(1H,3H,5H)-pyrimidinetrione
7 4-[(3,4-dihydroxy-5-cyanophenyl)methylidene]-2-thioxo-imidazolidin-5-one The following examples illustrate the preparation of the compounds according to the invention.

EXAMPLE 1

4-[(3,4-Dihydroxy-5-nitrophenyl)methylidene]-2-thioxoimidazolidin-5-one

A solution containing 2.9 g (0.025 mol) of 2-thiohydantoin, 4.6 g (0.025 mol) of 3,4-dihydroxy-5-nitrobenzaldehyde and 0.25 ml of piperidine in 50 ml of acetic acid was heated for 7–8 h at 100° C. The crystals were filtered and washed with 2-propanol. Yield 5.0 g (71%), mp>350° C. (decom.).

EXAMPLE 2

5-[(3,4-Dihydrozy-5-nitrophenyl)methylidene]-2-thioxothiazolidin-4-one

A solution containing 2.1 g (0.0157 mol) of rhodanine, 2.76 g (0.0151 mol) of 3,4-dihydrozy-5-nitrobenzaldehyde and 0.15 ml of piperidine in 10 ml of acetic acid was heated for 7–8 h at 100° C. After cooling the crystals were filtered and washed with 2-propanol. Yield 4.0 g (89%), mp>350° C. (decomp.).

EXAMPLE 3

5-[(3,4-Dihydroxy-5-nitrophonyl) methylidene]-thiazolidin-2,4-dione

A solution containing 0.59 g (0.005 mol) of thiazolidine-2,4-dione, 0.92 g (0.005 mol) of 3,4-dihydroxy-5-nitrobenzaldehyde and 0.05 ml of piperidine in 5 ml of acetic acid was heated for 7–8 h at 80° C. The crystals were filtered and washed with ethanol. Yield 1.0 g (72%), mp 295–298° C.

EXAMPLE 4

5-[(3,4-Dihydroxy-5-nitrophenyl)mothylidene]-2-aminothiazolidin-4-one

A solution containing 0.58 g (0.005 mol) of 2-aminothiazolidin-4-one, 0.92 g (0.005 mol) of 3,4-dihydrosy-5-nitrobenzaldehyde and 0.05 ml of piperidine in 5 ml of acetic acid was heated for 24 h at 100° C. The product was filtered and washed with ethanol. Yield 1.2 g (86%), mp 250° C. (decomp.).

EXAMPLE 5

5-[(3,4-Dihydroxy-5-nitrophenyl)methylidene]-4-thioxothiazolidin-2-one

A solution containing 0.67 g (0.005 mol) of 4-thioxothiazolidin-2-one, 0.92 g (0.005 mol) of 3,4-dihydroxy -5-nitrobenzaldehyde and 0.05 ml of piperidine in 10 ml of acetic was heated for 8 h at 100° C. The product was filtered and washed with 2-propanol. Yield 1.14 g (76.5%), mp>350° C. (decomp.).

EXAMPLE 6

5-[(3,4-Dihydroxy-5-nitrophenyl)mothylidene]-3-methyl-2-thioxothiazolidin-4-one

A solution containing 0.74 g (0,005 mol) of 3-methyl-2-thioxothiazolidin-4-one, 0.92 g (0.005 mol) of 3,4-dihydroxy-5-nitrobenzaldehyde, 0.05 ml of piperidine in 10 ml of acetic acid was heated for 8 h at 100° C. The product was filtered and washed with 2-propanol. Yield 0.87 g (56%), mp 274°–276° C.

EXAMPLE 7

5-[(3,4-Dihydroxy-5-nitrophenyl)methylidene]-2,4,6 (1H,3H,5H)-pyrimidinetrione.

To a solution containing 1.28 g (0.01 mol) of barbituric acid and 1.83 g (0.01 mol) of 3,4-dihydroxy-5-nitrobenzaldehyde in 20 ml of 2-propanol was gradually added 5.0 ml of thionyl chloride. The mixture was stirred for 100 h at room temperature. The product was filtered, washed with 2-propanol and recrystallized from acetic acid. Yield 1.28 g (44%), mp 269°–272° C.

EXAMPLE 8

4-[(3,4-Dihydroxy-5-nitrophenyl)methylidene]-2,5-imidazolidindione

A solution containing 0.65 g of hydantoin, 0.92 g of 3,4-dihydromy-5-nitrobenzaldehyde and 0.15 g of ammonium acetate in 15 ml of acetic acid was refluxed overnight. The product was filtered and washed with acetic acid and 2-propanol. Yield 0.56 g (42%), mp>350° C.

EXAMPLE 9

5-[(3,4-Dihydroxy-5-nitrophenyl)methylidene]-4-thioxo-2-oxazolidinone

A solution containing 0.25 g of 4-thioxo-2-oxazolone 0.38 g of 3,4-dihydroxy-5-nitrobenzaldehyde and 0.1 ml of piperidine in 5 ml of acetic acid was heated overnight at 100° C. The product was filtered and washed with actic acid. Yield 0.05 g, mp 245° C.

EXAMPLE 10

4-[(3,4-Dihydroxy-5-cyanophenyl)methylidene]-2-thioxoimidazolidin-5-one

A solution containing 0.58 g of thiohydantoin, 0.82 g of 3,4-dihydroxy-5-cyanobenzaldehyde and 0.1 ml of piperidine in 10 ml of acetic acid was heated for 4 h at 100° C. The product was filtered and washed with ether. Yield 0.51 g, mp 210°–213° C.

EXAMPLE 11

5-[(3,4-Dihydroxy-5-cyanophonyl)methylidene]-2-thioxothiazolidin-4-one

A solution containing 0.61 g of rhodanine, 0.72 g of 3,4-dihydroxy-5-cyanobenzaldehyde and 0.1 ml of piperidine in 10 ml of acetic acid was heated for 4 h at 100° C. The product was filtered and washed with 2-propanol. Yield 0.35 g, mp>350° C.

EXAMPLE 12

4-[(3,4-Dihydroxy-5-chlorophenyl)methylidene]-2-thiozoimidazolidin-5-one

A solution containing 1.16 g of thiohydantoin, 1.72 g of 3,4-dihydroxy-5-chlorobenzaldehyde and 0.2 ml of piperidine in 20 ml of acetic acid was heated for 4 h at 100 ° C. The product was filtered and washed with ether. Yield 1.0 g, mp 303°–304° C.

EXAMPLE 13

5-[(3,4-Dihydroxzy-5-chlorophenyl)methylidene]-thiazolidin-2,4-dione

A solution containing 1.33 g of thiazolidine-2,4-dione, 1.72 g of 3,4-dihydroxy-5-chlorobenzaldehyde and 2 ml of piperidine in 20 ml of acetic acid was heated for five hours at 100° C. Yield 1.9 g (70%), mp 299°–301° C.

EXAMPLE 14

5-[(3,4-Dihydroxy-5-nitrophenyl)methyl]-(1H,3H,5) pyrimidine-2,4,6-trione

To a suspension of 5-[(3,4-dihydroxy-5-nitrophenyl) methylidene]-(1H, 3H, 5H)pyrimidine-2,4,6-trione (example 7) (1 g) in water (30 ml) a solution of sodiumborohydride (2 g) in water (10 ml) was gradually added. The solution was stirred for 15 min at room temperature and acidified with 1N hydrochloric acid. The product was filtered and washed with water. Yield 0.7 g, mp 263°–6° C.

We claim:

1. A method for the prevention or treatment of tissue damage induced by lipid peroxidation in an animal or human in need of such prevention or treatment, said method comprising administering to said animal or human an effective antioxidant amount of a compound according to formula I

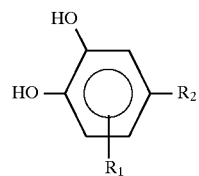

wherein $R_1$ is nitro, halogeno or cyano group and $R_2$ is a group selected from

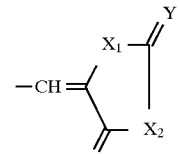

and

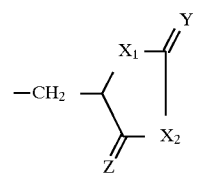

wherein Y and Z are independently oxygen, sulfur or NR, wherein R is hydrogen, straight or branched $C_{1-8}$alkyl, $C_{5-7}$-cycloalkyl, phenyl$C_{1-8}$alkyl or phenyl group; $X_1$ is NR, wherein R is hydrogen, straight or branched $C_{1-8}$alkyl, $C_{5-7}$cycloalkyl, phenyl$C_{1-8}$alkyl or phenyl group and $X_2$ is NR; or a pharmaceutically acceptable salt or ester thereof.

2. A method as claimed in claim 1, wherein the tissue damage is associated with heart disease, rheumatoid arthritis, cancer, an inflammatory disease, transplantation rejection reaction, ischemia or aging.

* * * * *